(12) United States Patent
Albertson et al.

(10) Patent No.: US 7,704,252 B2
(45) Date of Patent: Apr. 27, 2010

(54) STERNAL RECONSTRUCTION SYSTEM

(75) Inventors: Thomas Albertson, Phoenixville, PA (US); Christopher Goheen, New Cumberland, PA (US); Mark Michels, Glen Mills, PA (US)

(73) Assignee: Synthes USA, LLC, West Chester, PA (US)

( * ) Notice: Subject to any disclaimer, the term of this patent is extended or adjusted under 35 U.S.C. 154(b) by 1152 days.

(21) Appl. No.: 10/830,130

(22) Filed: Apr. 21, 2004

(65) Prior Publication Data
US 2005/0240198 A1 Oct. 27, 2005

(51) Int. Cl.
*A61B 17/82* (2006.01)

(52) U.S. Cl. .......................... 606/74; 606/905; 606/915

(58) Field of Classification Search ............. 606/69–74, 606/304, 323, 280, 286
See application file for complete search history.

(56) References Cited

U.S. PATENT DOCUMENTS

| | | | |
|---|---|---|---|
| 4,682,849 A * | 7/1987 | Kowata et al. ................ 385/39 |
| 5,190,545 A | 3/1993 | Corsi et al. |
| 5,318,566 A | 6/1994 | Miller |
| 5,320,663 A | 6/1994 | Cunningham |
| 5,345,663 A | 9/1994 | Scruggs |
| 5,361,475 A | 11/1994 | Scruggs |
| 5,741,260 A * | 4/1998 | Songer et al. ................ 606/74 |
| 5,766,218 A * | 6/1998 | Arnott ........................ 606/151 |
| 5,785,712 A | 7/1998 | Runciman et al. |
| 5,964,769 A * | 10/1999 | Wagner et al. ............... 606/74 |
| 6,158,437 A * | 12/2000 | Vagley ........................ 128/898 |
| 6,296,643 B1 | 10/2001 | Hopf et al. |
| 6,391,030 B1 * | 5/2002 | Wagner et al. ............... 606/74 |
| 6,436,123 B1 | 8/2002 | Magovern |
| 6,544,267 B1 * | 4/2003 | Cole et al. ................... 606/74 |
| 7,065,267 B2 * | 6/2006 | Zhong et al. ................. 385/15 |
| 2002/0091391 A1 * | 7/2002 | Cole et al. ................... 606/72 |
| 2005/0038428 A1 * | 2/2005 | Kelman et al. ............... 606/60 |
| 2005/0171547 A1 * | 8/2005 | Aram .......................... 606/74 |
| 2005/0222575 A1 | 10/2005 | Ciccone et al. |

OTHER PUBLICATIONS

Chase, C.W. et al., "Internal Fixation of the Sternum in Median Sternotomy Dehiscence," Plastic and Reconstructive Surgery, May 1999, 1667-1673.

* cited by examiner

*Primary Examiner*—Thomas C Barrett
*Assistant Examiner*—Michael J Araj
(74) *Attorney, Agent, or Firm*—Woodcock Washburn LLP (57) ABSTRACT

A sternal reconstruction system for securing parts of a sternum includes at least one flexible cable with crimp fitting, at least one cannulated screw and at least one reconstruction plate. Circumferential or parasternal fixation may be brought about by use of a sternal reconstruction system including a flexible cable and crimp fitting alone; a sternal reconstruction system including a flexible cable, crimp fitting and cannulated screws; or a system including a flexible cable, crimp fitting, cannulated screws and one or more reconstruction plates. The reconstruction plates are typically planar, having an upper and a lower surface, and containing generally perpendicular and transverse plate holes. The generally perpendicular plate holes are countersunk to better accommodate the heads of the cannulated bone screws. Also provided is a kit for sternal reconstruction.

53 Claims, 10 Drawing Sheets

STERNAL RECONSTRUCTION SYSTEM

FIELD OF THE INVENTION

The present invention relates generally to surgical reconstruction systems or devices, and more particularly, to devices for reapproximating two or more parts of a patient's sternum.

BACKGROUND OF THE INVENTION

Many surgical procedures require two or more parts of a sternum to be reapproximated, or fixed together, such as sternal reconstruction and repair of sternal trauma. In addition, various types of surgical procedures are currently performed to investigate, diagnose, and treat diseases involving tissues or organs located in a patient's thoracic cavity, such as the heart and lungs. These procedures typically require a partial or median sternotomy to gain access to the patient's thoracic cavity. A partial or median sternotomy is a procedure by which a saw or other appropriate cutting instrument is used to make a midline, longitudinal incision along a portion or the entire axial length of the patient's sternum, allowing two opposing sternal halves to be separated laterally. A large opening into the thoracic cavity is thus created, through which a surgeon may directly visualize and operate upon the heart and other thoracic organs, vessels, or tissues. Following the surgical procedure within the thoracic cavity, the two severed sternal halves must be reapproximated.

Various types of orthopedic devices are known for the reapproximation or fixation of bone fragments such as sternal halves. Such devices typically are used to stabilize bones by maintaining fractured bone portions in relatively fixed positions with respect to each other. The alignment and stability provided by the devices promotes the healing of fragments, allowing proper fusion to occur.

Internal fixation devices include bone screws, which are used in a variety of orthopedic applications for fixation of bone fragments. Bone fragments may be positioned in a desired configuration, and one or more holes may be drilled and tapped across the fracture. Compression and stabilization of the bone fragments may then be effected by screwing bone screws into the holes. One limitation associated with bone screws, however, is that repositioning or adjusting the bone screws following implantation is difficult. In order to accommodate a different alignment, it is often necessary to remove the original bone screws and drill new holes for subsequent bone screw implantation.

Metal pins also are often used to stabilize bones. Similar to bone screws, metal pins may be inserted in holes drilled across bone fragments to confer stability to the bone. However, as with bone screws, removal of the pins may be required if subsequent realignment of bone portions is necessary.

Bone plates are fastenable to the surface of a bone typically at both sides of a fracture to support and/or stabilize the fragments. Bone plates have typically been attached to the bone with bone screws that extend from the plate into the bone. In some examples, the head of the bone screw is locked to the plate (e.g., by threaded engagement between the screw head and the bone plate) and in other plates the head of the screw is free to angulate with respect to the plate, such that the screw may be placed in the bone at a surgeon-selected angle. In yet other examples, the screw head may cooperate with the bone plate to provide compression or distraction of the fragments (i.e., to push the bone fragments towards or away from one another).

Intramedullary implants are another device used for fixation of bone fragments. Such a device may be placed in the central canal of a fractured bone and locked thereto at the longitudinal ends of the device using screws. The use of intramedullary implants is very invasive, though, and the implants are difficult to manipulate once installed within the canals of bone fragments.

External fixation devices also are commonly used to stabilize bone segments. These devices employ a plurality of pins which extend through a patient's skin into holes drilled in fractured bone. Clamps are used to secure the pins to a common apparatus, which may for example take the form of a rod that is disposed generally parallel to the anatomically correct longitudinal axis of the fractured bone. The clamps in combination with the common apparatus create a rigid frame for immobilizing the fracture to promote healing.

External skeletal fixation is a preferred method of treatment for various limb deformities, injuries, and other conditions including: severe open fractures, fractures associated with severe burns, fractures requiring distraction, fractures requiring limb lengthening, arthrodesis, infected fractures, and nonunions. External fixation offers several advantages over the above-mentioned internal fixation approaches. For example, external fixation enables skeletal stabilization to be managed from a location that is generally remote from the deformity, injury, or disease, thereby permitting direct surveillance of the limb and wound during related or subsequent procedures. In addition, external fixation facilitates adjustment of fracture alignment, bone lengthening, bone compression, and fixed distraction following initial surgery. Furthermore, minimal interference with proximal and distal joints allows immediate mobilization of a wounded limb, and insertion of the fixator pins can be performed under local anesthesia.

Despite these developments, there remains a need for fixation devices with improved adjustability and selectivity.

SUMMARY OF THE INVENTION

The present invention is directed to a sternal fixation device for securing parts of a sternum. The sternal reconstruction system for securing parts of a sternum comprises a flexible cable having first and second ends; a crimp fitting member; optimally at least one cannulated screw; and optimally at least one reconstruction plate. The reconstruction plate has a longitudinal axis and comprises an upper and a lower surface, at least one hole passing through the upper and lower surfaces and generally perpendicular to the longitudinal axis for receiving a fastener head, and may further include at least one hole disposed transverse to the perpendicularly disposed plate hole.

According to one aspect of the invention, the sternal reconstruction system comprises at least one reconstruction plate comprising a plurality of holes passing through the upper and lower surfaces and generally perpendicular to the longitudinal axis for receiving fastener heads, and a plurality of holes disposed transverse to the generally perpendicularly disposed plate holes. In one embodiment the plurality of holes passing through the upper and lower surfaces and generally perpendicular to the longitudinal axis are countersunk. The upper and lower surfaces of the reconstruction plate are preferably planar.

According to another aspect of the invention, the sternal reconstruction system comprises at least one cannulated screw selected from the group consisting of a locking and a non-locking screw. In one embodiment the cannulated screw is constructed from stainless steel, titanium, an alloy of titanium or a resorbable material, and is at least partially threaded for attachment to bone.

According to another aspect of the invention, the sternal reconstruction system comprises a flexible cable having first and second ends. The cable is selected from the group consisting of a single strand wire and a multi-wire stranded cable. In one embodiment the flexible cable is Cerclage wire. In another embodiment the first end of the cable comprises a preinstalled flattened crimp fitting. In a further embodiment the second end of the cable comprises a suture. The suture and the cable may be constructed from any suitable bio-compatible material, including, but not limited to, stainless steel, titanium, alloys of titanium and resorbable materials.

The present invention also relates to a method for sternal reconstruction comprising the steps of wrapping a flexible cable around the sternum for fixation; reapproximating the separated parts of the sternum; tensioning the flexible cable; and securing the tensioned cable. The tensioned cable may be secured by use of a crimp fitting.

The present invention also relates to a method for sternal reconstruction comprising the steps of inserting at least one cannulated screw into the sternum; feeding flexible cable through the lumens of the cannulated screws; tensioning the flexible cable to a desired tension, and securing the tensioned cable. In one embodiment at least one cannulated screw is inserted into the sternum on the opposite sides of the sternal fracture. In another embodiment the cannulated screws prevent the flexible cable or wire from bearing directly on the soft bone of the sternum.

The present invention also relates to a method for sternal reconstruction comprising the steps of attaching at least one reconstruction plate to a sternum using cannulated screws, wherein said reconstruction plate has a longitudinal axis and comprises an upper and a lower surface, and at least one hole passing through the upper and lower surfaces and generally perpendicular to the longitudinal axis for receiving a fastener head, the at least one reconstruction plate further including at least one hole disposed transverse to the generally perpendicularly disposed plate hole; feeding flexible cable through the lumens of the cannulated screws and/or through the at least one hole disposed transverse to the generally perpendicularly disposed plate hole; tensioning the flexible cable to a desired tension, and securing the tensioned cable. In one embodiment at least one reconstruction plate is attached to the sternum on each of the opposite sides of the sternal fragments. The transverse holes are preferably located between the generally perpendicularly disposed plate holes and may be smaller than the generally perpendicularly disposed holes, and are sized to allow the cable to be inserted therethrough.

The present invention also relates to a sternal reconstruction kit which comprises at least one flexible cable, at least one cannulated screw and at least one reconstruction plate. Optionally the kit may contain at least one flexible cable which has attached at one end a suture. The kit may optionally comprise a plurality of sizes of cannulated screws and/or a plurality of sizes of reconstruction plates.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

The sternal reconstruction system of the present invention comprises a flexible cable with crimp, optionally one or more cannulated screws and optionally one or more reconstruction plates. In one embodiment of the present invention, simple circumferential or parasternal fixation may be provided by use of a sternal reconstruction system comprising a flexible cable and ferrule. In another embodiment, fixation may be achieved by use of a sternal reconstruction system comprising a flexible cable, crimp and cannulated screws. In yet another embodiment, fixation may be achieved by use of a sternal reconstruction system comprising a flexible cable, crimp, cannulated screws and one or more reconstruction plates.

While various descriptions of the present invention are described in the Figures, it should be understood that the various features described are for illustrative purposes, and are exemplary only. Therefore, this invention is not to be limited to only the specifically preferred Figures depicted herein.

Figure 1:
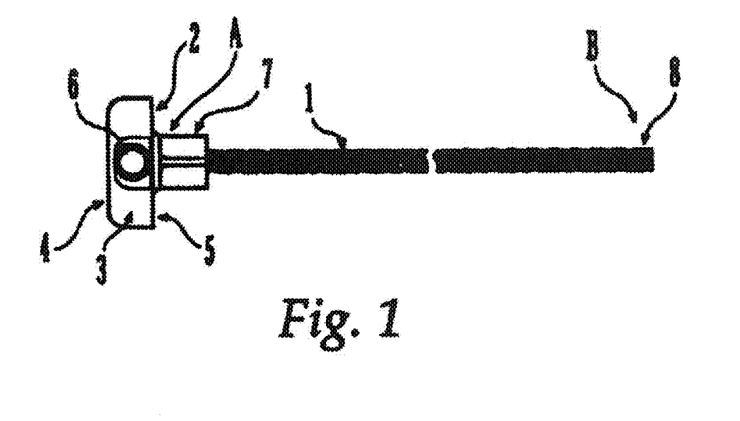
FIG. 1 is a perspective view of a first embodiment of a sternum reconstruction flexible cable with preinstalled flattened round crimp fitting.
Figure 2:
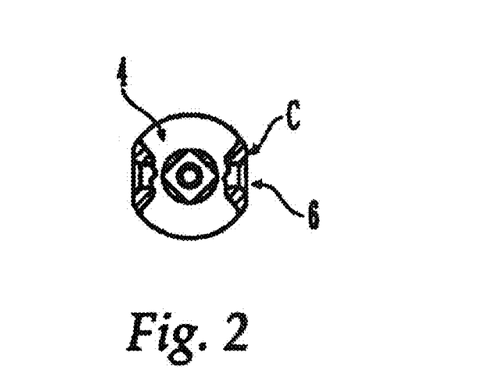
FIG. 2 is an end-view, partial cross-section of crimp fitting.
Figure 3A:
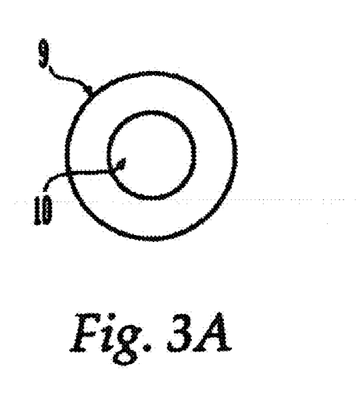
FIG. 3A is an end view of a cylindrical ferrule.
Figure 3B:
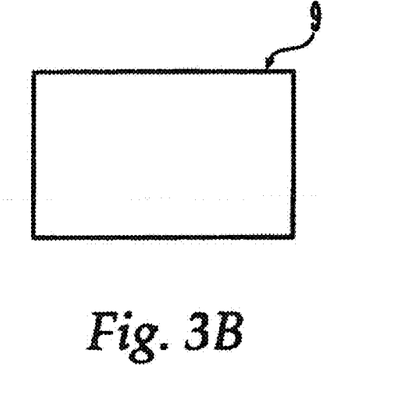
FIG. 3B is a side view of a cylindrical ferrule.

A first illustrative embodiment of a sternal reconstruction system is shown in FIGS. 1 to 3. The sternal reconstruction system shown in FIG. 1 comprises a flexible cable 1 having two ends, a first end A having attached thereto a crimp fitting 2, and a second end B consisting of a thermally fused end 8. Thermally fused end 8 may assist in threading flexible cable 1 through the other elements of the sternal reconstruction system, and may also assist in preventing unraveling of flexible cable 1. Flexible cable 1 can be a single strand wire or a multi-wire stranded cable having from about 2 to about 1000 strands, preferably from about 50 to about 300 strands and most preferably from about 110 to about 145 strands, and has first and second ends A, B. Flexible cable 1 may have any suitable degree of flexibility from highly flexible like yarn to stiff like wire. The flexible cable 1, however, is sufficiently flexible to readily conform to the sternum, while sufficiently rigid to be manipulated as required. Flexible cable 1 is typically attached to crimp fitting 2 by crimping the fitting onto the cable. Crimp fitting 2 may be constructed from any suitable bio-compatible material, including, but not limited to, titanium, alloys of titanium, stainless steel and resorbable materials, although one of ordinary skill in the art will know and appreciate that any biocompatible material may be used.

Crimp fitting 2 preferably comprises a preinstalled flattened disk-like crimp head 3 having an upper surface 4 and a lower surface 5. Upper surface 4 may be flat or curved and optionally has rounded edges. Lower surface 5 preferably is designed so as to mate with the top surface of a cannulated screw and/or a reconstruction plate, resulting in greater stability and/or a low profile. The flat lower surface 5 may assist in stabilizing the crimp fitting to a bone anchor, such as a screw, or to a bone plate, and results in greater stability of the system. In addition, the flat lower surface helps provide a low profile to the crimp fitting. Crimp head 3 has a diameter of from about 2 mm to about 10 mm, preferably about 6 mm, and a thickness of from about 0.1 mm to about 4 mm, preferably about 2 mm. While crimp head 3 is preferably a round disk, it may have other shapes such as square, rectangular or other polygon shape. Crimp head 3 has a diametrical hole or bore 6 through which the second or thermally fused end 8 of the flexible cable 1 is passed for attachment after the cable 1 is looped around the sternum. Diametric hole or bore 6 is sized so as to be able to accommodate the flexible cable 1, and preferably has a diameter of from about 0.7 mm to about 2.5 mm, and more preferably about 1 mm.

Crimp fitting 2 further comprises a crimp shaft 7 that extends generally perpendicular to lower surface 4. Crimp shaft 7 may be cylindrically shaped, or have a non-circular cross-section. The crimp shaft 7 may be a cylindrical tube which has an opening that receives the first end A of the flexible cable 1. The cylindrical tube may thereafter be crimped to attach the flexible cable 1 to the crimp fitting 2. The crimping process of the crimp shaft 7 may form a non-circular shape in the crimp shaft 7, or other desired shape. The crimp shaft 7 is located on the lower surface 4 of the crimp head such that the perimeter of the lower surface 4 of the crimp head surrounds the crimp shaft 7 in order to provide an annular bearing surface C. Annular bearing surface C has a width of from about 0.5 mm to about 3 mm. Preferably the crimp shaft 7 projects perpendicularly from the lower surface 4 of the crimp head 3. Crimp shaft 7 preferably is sized and shaped so as to fit within a cannulated screw or a bone plate. The non-circular cross-section of the crimp shaft 7 may engage the non-circular recess formed in a cannulated screw to prevent rotation of crimp fitting 2 in the cannulated screw. Crimp shaft 7 preferably may range in size from about 0.7 mm to about 4 mm in diameter, more preferably about 2.5 mm, and from about 1.5 mm to about 4 mm in length, more preferably about 3 mm. Preferably the diameter of crimp shaft 7 should not be less than the diameter of flexible cable 1. The length and shape of crimp shaft 7 may assist in stabilizing the crimp fitting 2 to a bone anchor, such as a screw, or to a bone plate, and results in greater stability of the system.

FIG. 2 shows an end view, partial cross-section of the upper face 4 of the crimp fitting 2. Diametric hole 6 may have an included counter sink region D on both sides of the crimp head 3 where it opens to the exterior. FIG. 3A shows an end view of a cylindrical ferrule 9 which contains a hole 10 along its longitudinal axis. FIG. 3B shows a side view of the ferrule. The hole 10 along the longitudinal axis of the ferrule 9 is sized so as to accommodate the flexible cable 1. The inner diameter of the ferrule 9 may have a sharp edge in order to facilitate the cutting of the flexible cable 1 during crimping of the ferrule 9 onto the flexible cable 1. Ferrule 9 may be constructed from any suitable bio-compatible material, including, but not limited to, titanium, alloys of titanium, stainless steel and resorbable materials, although one of ordinary skill in the art will know and appreciate that any biocompatible material may be used. In an illustrative embodiment, cylindrical ferrule 9 can be crimped onto the flexible cable 1 after flexible cable 1 is drawn through diametric hole 6 to a predetermined tension. The ferrule 9 preferably is sized so that it can not fit through the diametric hole 6, preferably at least after it is crimped onto the flexible cable 1. In another embodiment, ferrule 9 may be secured onto the flexible cable 1 by an adhesive. One of ordinary skill in the art will know and appreciate that any suitable biocompatible adhesive may be used. In another embodiment, flexible cable 1 and/or ferrule 9 are constructed from resorbable materials, and ferrule 9 may be secured onto the flexible cable 1 by thermal fusing.

Figure 4:
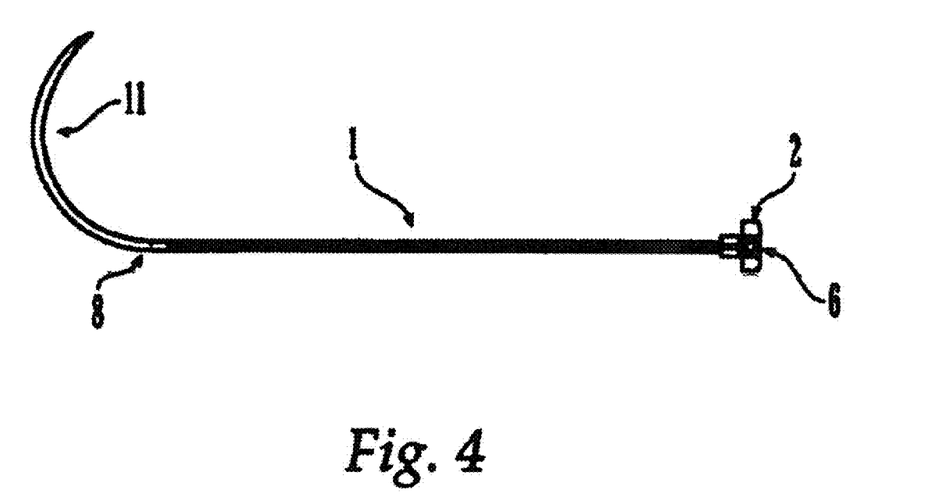
FIG. 4 is a side view of a flexible cable with crimp fitting at one end and a suture at the other end.

Another illustrative embodiment of a sternal reconstruction system is shown in FIG. 4. In this embodiment, the second or thermally fused end 8 of the flexible cable 1 may be attached to a suture or needle 11. The suture 11 may typically be removed following its use, and is designed to be removed while preserving the fused end of the cable 1. The suture 11 may be constructed from any suitable bio-compatible material, including, but not limited to, titanium, alloys of titanium and stainless steel, although one of ordinary skill in the art will know and appreciate that any biocompatible material may be used.

The flexible cable 1 and crimp fitting 2 may be used to reapproximate, or secure together, two or more parts of a sternum by placing the crimp fitting 2 against a sternum to be mended and the flexible cable 1 wound around the separate portions of the sternum. The second or thermally fused end 8 of the flexible cable 1 to be attached to the crimp fitting 2 is pulled to bring the flexible cable 1 taut around the sternum, thus reapproximating the separated parts of the sternum. The second or thermally fused end 8 of the flexible cable 1 is passed through the diametrical hole 6, and the flexible cable 1 is pulled taut. The tensioning of the flexible cable 1 may be carried out, for example, by use of a safety cable tool. When the desired tension is achieved, the flexible cable 1 is secured in place by the ferrule 9. Attachment of the ferrule 9 to the flexible cable 1 may be carried out, for example, by crushing with pliers or any suitable crimping instrument. In an illustrative embodiment, a cylindrical ferrule 9 (FIG. 3) can be crimped onto the flexible cable 1 after the cable 1 is drawn through the hole 6 in crimp head 3 to a predetermined tension.

The flexible cable 1 has a diameter of from about 0.7 mm to about 2.5 mm. Typically, if the flexible cable 1 is constructed of non-resorbable materials, it has a diameter of from about 0.7 mm to about 1.5 mm. Preferably flexible cable 1 has a diameter of about 1 mm. In one embodiment of the invention the flexible cable is Cerclage wire. The flexible cable 1 may be of any suitable length, and is preferably from about 10 cm to about 1.5 m in length. Flexible cable 1 may be constructed from any suitable bio-compatible material, including, but not limited to, titanium, alloys of titanium, stainless steel and resorbable materials, although one of ordinary skill in the art will know and appreciate that any biocompatible material may be used.

Figure 5:
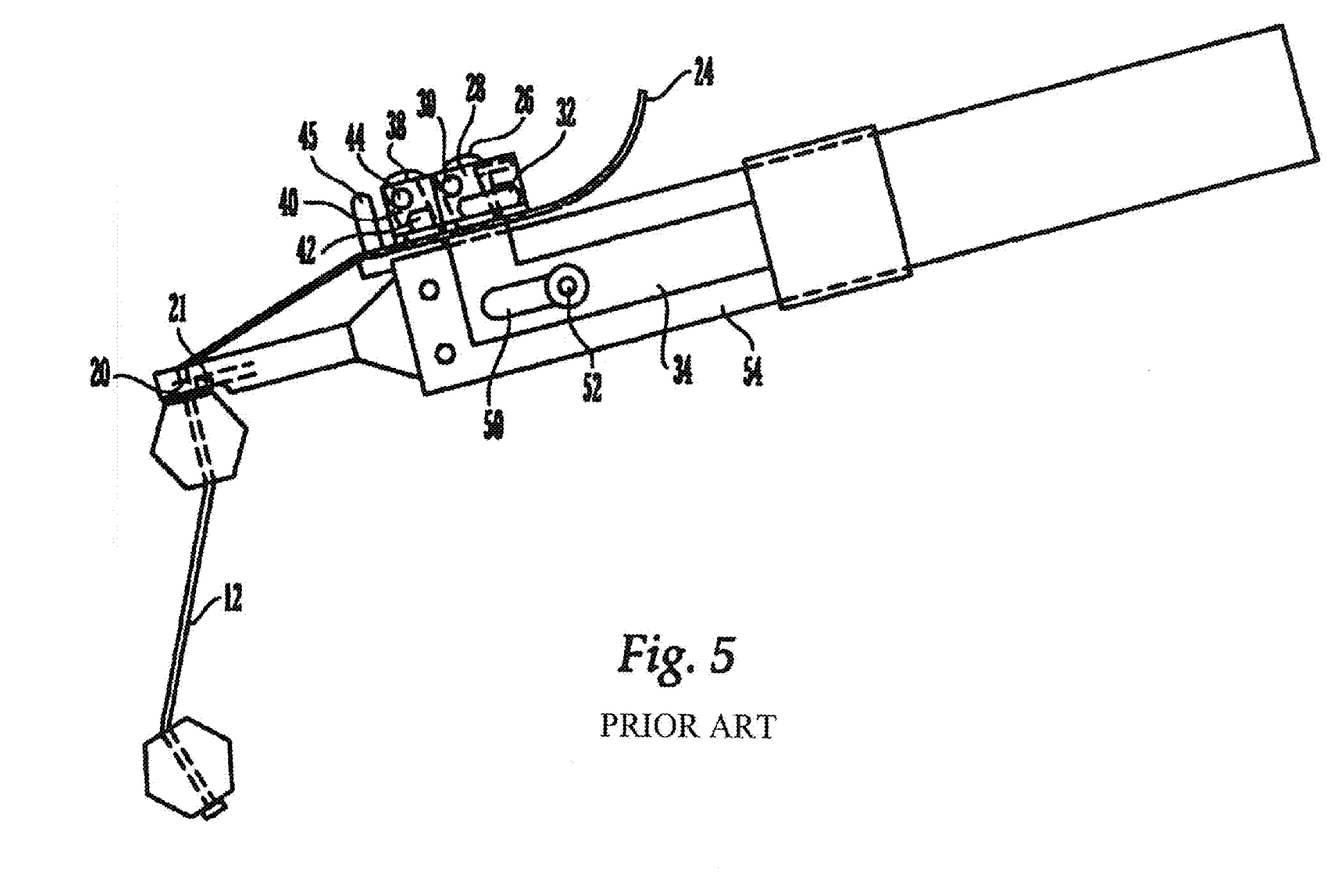
FIG. 5 is a perspective view of a safety cable tool.
Figure 6:
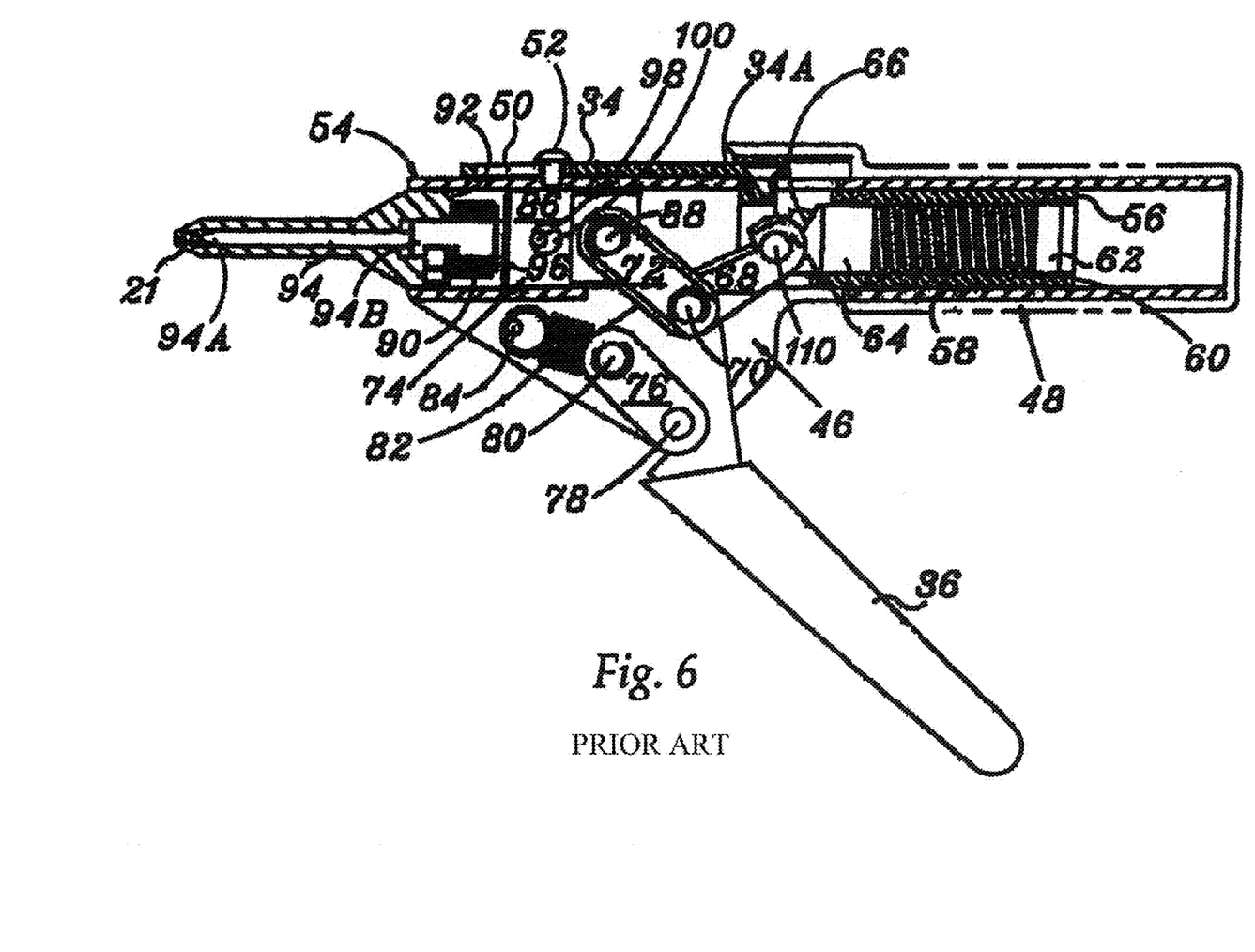
FIG. 6 is a cross-sectional view of a safety cable tool.

FIGS. 5 and 6 show a safety cable tool. The safety cable tool can be used for tensioning the flexible cable or wire 1 used with the sternal reconstruction system. The tool can be used to grasp and pull a flexible cable 1 to a predetermined tension limit. At the predetermined tension, the tool can be used to crimp a ferrule 9 to secure the flexible cable 1. The tool may also be used to sever the unused portion of flexible cable 1. The crimping and severing processes may be carried out independently or simultaneously, and manually or automatically. FIG. 5 shows a ferrule 20 seated in aperture 21 of the safety cable tool. A cable 12 with free end 24 is passed through the ferrule and through a clamping assembly 26 connected to a reciprocal arm 34. The cable 12 is also connected to a second clamping assembly 38. The clamping assemblies include pawls 28 and 40, which allow movement of the cable only in the direction of the cable's free end 24.

FIG. 6 shows an exploded perspective of the safety cable tool. Upon depression of handle 36 toward housing 54, handle 36 pivots about pin 80 and forces pin 70 to move upwards. As pin 70 goes up, arm 68 rotates clockwise about pin 110 and arm 72 rotates counterclockwise about pin 88, forcing pins 88 and 110 apart. Pin 110 is linked to reciprocal arm 34. As pin 110 moves away from pin 88, pressure is applied to move reciprocal arm 34 against the bias of spring 58, putting tension on cable 12. When the tension on cable 12 equals the bias of spring 58, pin 110 will move no farther and depressing handle 36 forces pin 88 to move toward the aperture 21. Pin 110 is also linked to a plunger 94 such that when pin 88 is forced in the direction of the aperture 21, plunger end 94A is pushed into aperture 21, thereby crimping the ferrule 20 about the cable 12 and simultaneously cutting cable 12 on the free end side of the ferrule. Suitable safety cable tools are commercially available from Daniels Manufacturing Corporation and are described in U.S. Pat. Nos. 5,320,663; 5,345,663; and 5,361,475, the contents of which are incorporated herein in their entirety.

In one embodiment of the sternal reconstruction system, one end of the cable 1 comprises a preinstalled flattened round crimp fitting 2 with a diametrical hole 6 through which the second or thermally fused end 8 of the flexible cable 1 may pass after the cable 1 is looped around the sternum or passes through the cannulated screw 13. In this embodiment, the separated parts of the sternum may be reapproximated by tensioning the flexible cable 1 to a desired tension, and securing the cable 1 by crimping. In one embodiment, a cylindrical ferrule 9 may be crimped onto flexible cable 1 after the cable 1 is drawn through a cannulated screw and the diametric hole 6 in crimp fitting 2 to the preselected desired tension. The safety cable tool described above may be used to achieve such tensioning and crimping.

Figure 7:
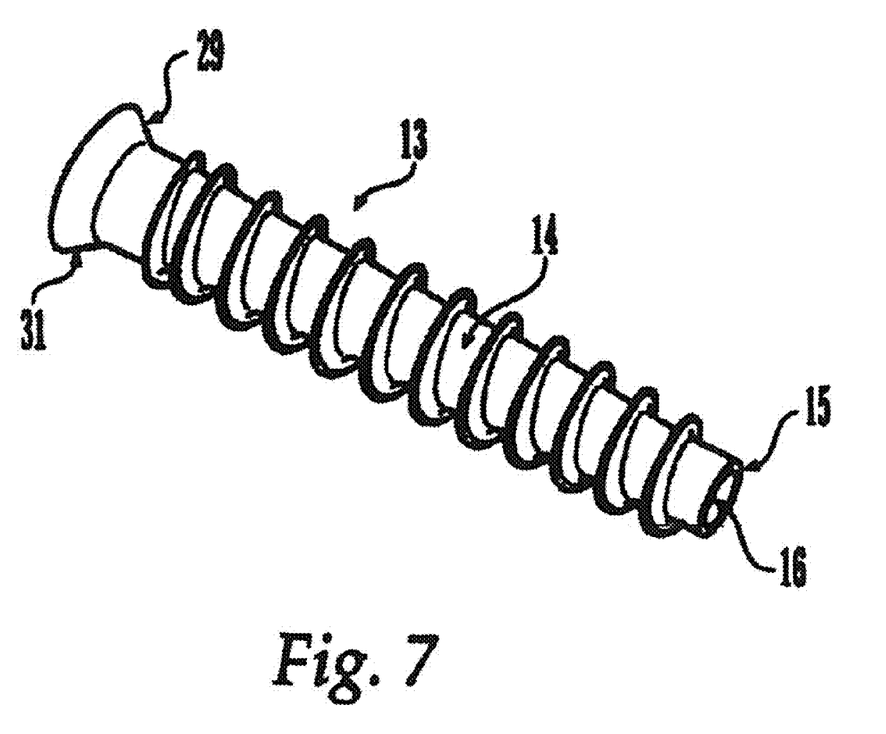
FIG. 7 is a top view of a cannulated screw.

In another illustrative embodiment, the sternal reconstruction system comprises flexible cable 1, crimp fitting 2 and at least one cannulated screw 13. FIG. 7 shows cannulated screw 13, having a shaft 14 that is at least partially threaded for attachment to bone. The length of shaft 14 and the shaft thread configuration is selected to be suitable for use in the sterna. As is well known in the art, the threads and a tip 15 can be made to be self-tapping and/or self-drilling to facilitate implantation. Shaft 14 has a diameter of from about 1 mm to about 5 mm, and is cannulated with a channel or throughbore 16 for receiving the flexible cable 1 to aid in fixation of the sternum. The diameter of throughbore 16 is preferably from about 0.7 mm to about 2.5 mm, and more preferably about 1 mm. The head 29 of the cannulated screw 13 preferably has a flat or curved under surface 31 which will bear against a reconstruction plate (if used) or the anterior side of the sternum.

Figure 8:
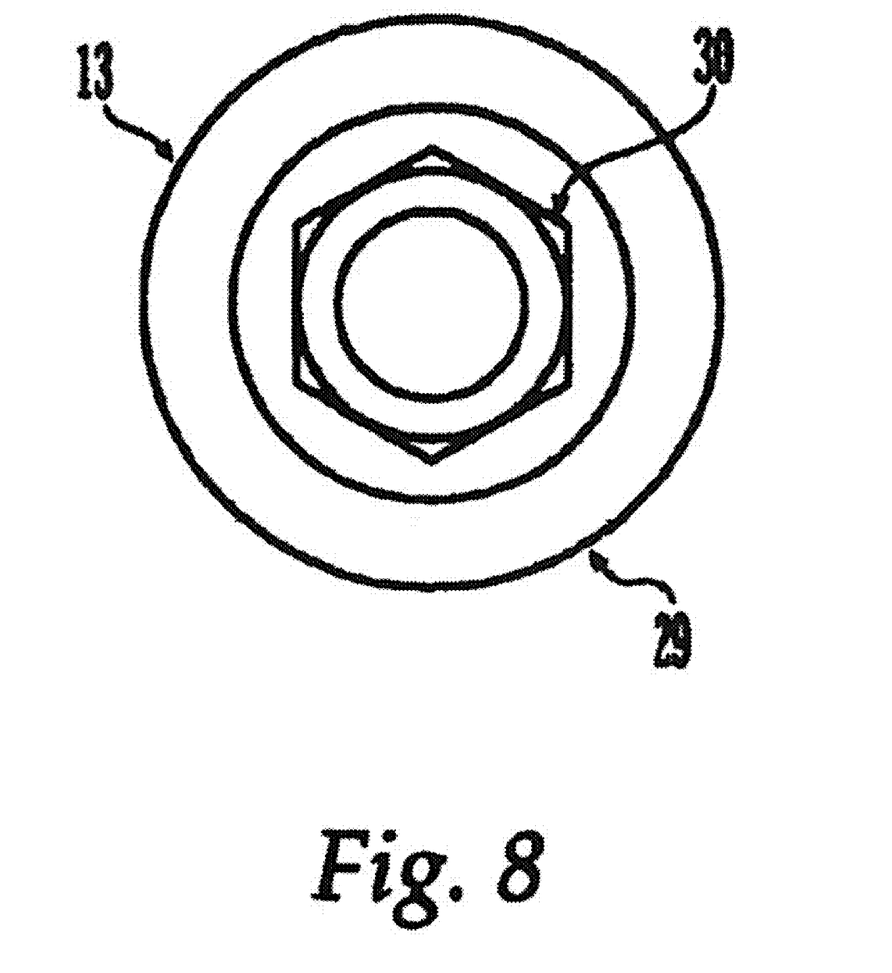
FIG. 8 is an end view of a cannulated screw.
Figure 9:
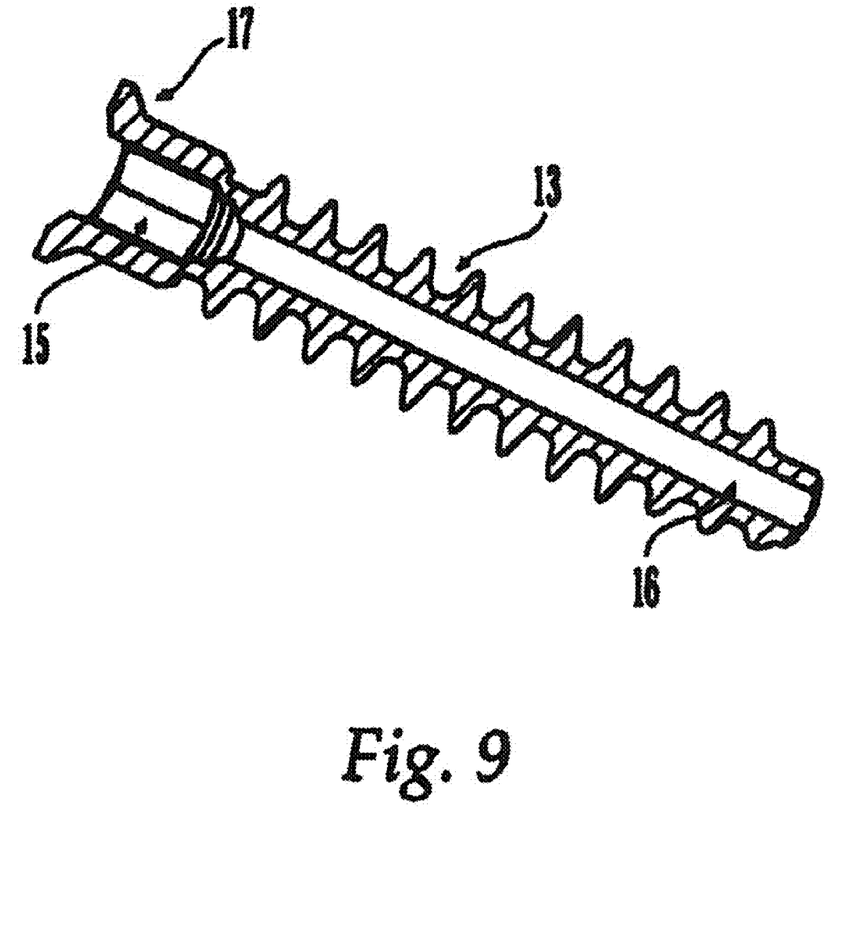
FIG. 9 is an exploded side view of a cannulated screw.

Further illustrative embodiment of a cannulated screw 13 are shown in FIGS. 8 and 9. As shown in FIG. 8, which shows an end view of cannulated screw 13, the head 29 of the cannulated screw 13 may comprise an internal hex 30 for receiving an installation tool. An installation tool for use in drilling a hole in bone and for driving any of a variety of cannulated fasteners into the drilled hole is further described in pending U.S. application Ser. No. ______ entitled "Adjustable Tool for Cannulated Fasteners," by Ciccone et al., which is incorporated by reference herein in its entirety. The diameter of internal hex 30, measured as the distance between opposite faces, is from about 1.5 mm to about 4 mm, and more preferably about 2.5 mm. FIG. 9 shows a cross-sectional view of cannulated screw 13, and shows that the head 29 of the cannulated screw 13 comprises a hollow aperture 15, while the shaft of the cannulated screw 13 is cannulated with a throughbore 16 which may receive the flexible cable 1. The head 29 of the cannulated screw 13 has a top surface that may be curved, substantially flat or other complex geometry. In one embodiment, the lower surface 4 of the crimp fitting 2 has a geometry that compliments the top surface of the screw 13 or reconstruction plate 18 to assist in stabilizing the crimp fitting 2 in location on the screw 13 or reconstruction plate 18. The hollow aperture 15 is preferably sized and shaped so as to accommodate crimp shaft 7. The matching of the size and shape of crimp shaft 7 to the hollow aperture 15 may result in greater stability of the crimp fitting 2 in the screw 13, particularly if there is a close fit between the shaft 7 and aperture 15. In this manner the crimp shaft 7 may act as a journal inside the screw aperture 15. The flat lower surface 5 of the crimp fitting 2 preferably sits flush to the head of the cannulated screw 13, and also provides stability to the system. In general, any surgical screw as described above, having a threaded or a non-threaded head 17 of an appropriate size and geometry for select plate holes of the bone plate can be used. The head 29 of cannulated screw 13 may be configured to lock with an optimally supplied bone plate or to be a non-locking screw. The head 29 of cannulated screw 13 has a diameter of from about 2 mm to about 10 mm, and preferably about 6 mm.

The cannulated screws 13 may be constructed from any suitable bio-compatible material, including, but not limited to, titanium, alloys of titanium, stainless steel and resorbable materials, although one of ordinary skill in the art will know and appreciate that any biocompatible material may be used. The cannulated screws 13 may be of any suitable length, and are typically from about 5 mm to about 24 mm in length. The skilled artisan will know that a screw 13 should be selected preferably so as to have a length such that, on use in sternal reconstruction, the tip of screw 13 will extend up to the posterior surface of the sternum, but preferably will not protrude to an undesirable distance from the posterior of the sternum.

In one embodiment of the invention, the cannulated screws 13 are inserted into the sternum on opposite sides of the sternal fragments. Flexible cable or wire 1 is fed through the lumen 16 of the cannulated screws 13, and is tensioned to a desired tension, causing the portions of the sternum to be brought together. The tensioned flexible cable 1 is secured to secure the aligned sternum. The cannulated screws 13 prevent the flexible cable or wire 1 from bearing directly on the soft bone of the sternum, thus alleviating the clinical problems of "cut through" and sternal dehiscence, or separation of the bony sternum and manubrium following median sternotomy.

Figure 10:
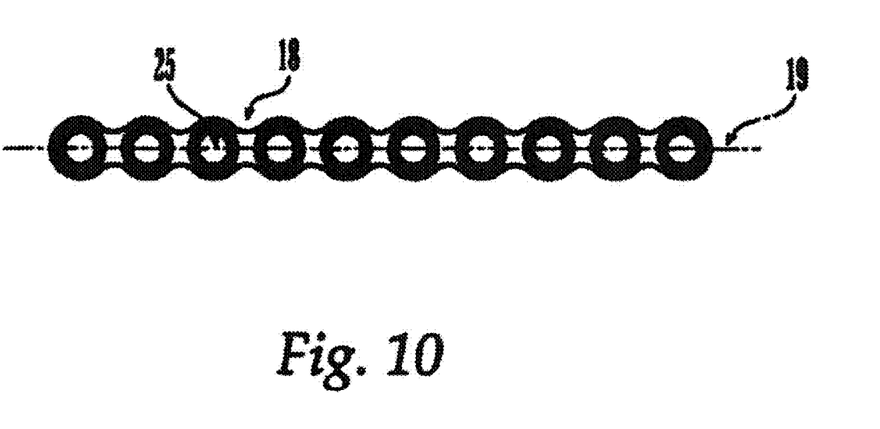
FIG. 10 is an overhead view of a reconstruction plate.

In another illustrative embodiment, the sternal reconstruction system comprises flexible cable 1, crimp fitting 2, cannulated screws 13 and at least one bone reconstruction plate 18. FIGS. 10 to 13 show illustrative embodiments of the reconstruction plate 12. FIG. 10 shows a top view of reconstruction plate 18, having a generally rectangular cross section. However, any suitable configuration for the reconstruction plate 18 could be used. The reconstruction plate 18 has a longitudinal axis 19, upper and lower surfaces 22, 23, at least one plate hole 25 disposed generally perpendicularly to the longitudinal axis 19 of the reconstruction plate 18, and at least one plate hole or bore 26 disposed transverse to the generally perpendicularly disposed plate hole 25. Generally perpendicular plate holes 25 are each independently angled at a solid angle of from 0° to about 30° from normal to the upper and lower surfaces of the plate 18. Preferably, perpendicular plate holes 25 are each independently angled at an angle of from 0° to about 30° from normal to the upper and lower surfaces of the plate 18 and along longitudinal axis 19. Most preferably, generally perpendicular holes 25 are normal to the upper and lower surfaces of the plate 18, i.e., at 0°. Transverse plate holes or bores 26 are each independently angled at a solid angle of from 0° to about 30° from normal to the side surfaces of the plate 18. Preferably, transverse plate holes or bores 26 are each independently angled at an angle of from 0° to about 30° from normal to the side surfaces of the plate 18 and transverse to longitudinal axis 19. Most preferably, transverse holes or bores 26 are normal to the side surfaces of the plate 18, i.e., at 0°. Reconstruction plate 18 has a length of from about 30 mm to about 250 mm, more preferably from about 80 mm to about 200 mm; a width of from about 5 mm to about 20 mm, more preferably from about 6 mm to about 10 mm; and a thickness of from about 0.5 mm to about 10 mm, more preferably from about 2 mm to about 4 mm. Plate holes 25 extend from the upper surface 22 through the lower surface 23 of the reconstruction plate, and can be optionally used for accommodating fasteners, e.g. cannulated screws 13, pins, and/or flexible cable 1, to secure the reconstruction plate 18 to the sternum.

Plate holes 26 extend transversely through the longitudinal axis 19 of the reconstruction plate 18, and can optionally also be used for accommodating fasteners, e.g. cannulated screws and/or flexible cable, to secure the reconstruction plate to the sternum. The transverse holes 26 are preferably located between generally perpendicular holes 25. Any suitable combination of fasteners, such as, for example, cannulated screws 13 or other screws, blades, nails, pins, etc. may be used to secure the reconstruction plate 18 to the sternum; for example, in one embodiment, bone anchors may be used solely with the generally perpendicular plate holes 25, while in another embodiment flexible cable such as cable 1 and crimp fitting 2 solely may be used with the transverse plate holes 25. In a preferred embodiment, a combination of generally perpendicular and transverse plate holes 25, 26 is selected so as to give optimum local securing of the reconstruction plates 18. In a preferred embodiment, the reconstruction plate 18 comprises a plurality of plate holes 25 disposed generally perpendicularly to the longitudinal axis 19 of the reconstruction plate 18, and a plurality of plate holes 26 disposed transverse to the generally perpendicularly disposed plate holes 25.

Figure 11:
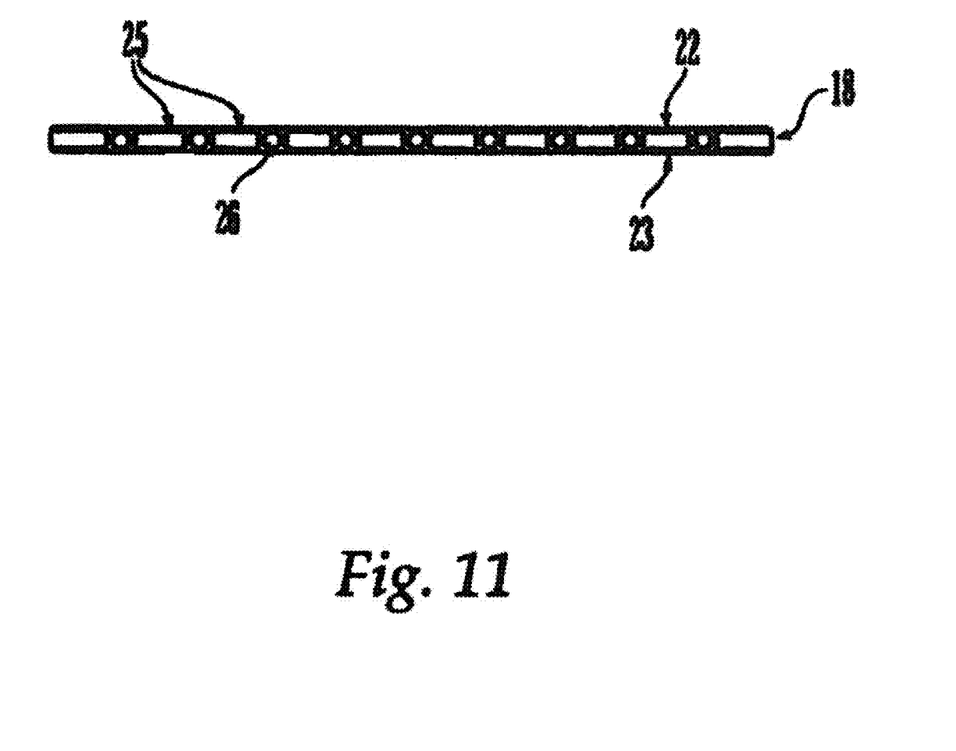
FIG. 11 is a side view of a reconstruction plate.
Figure 12:
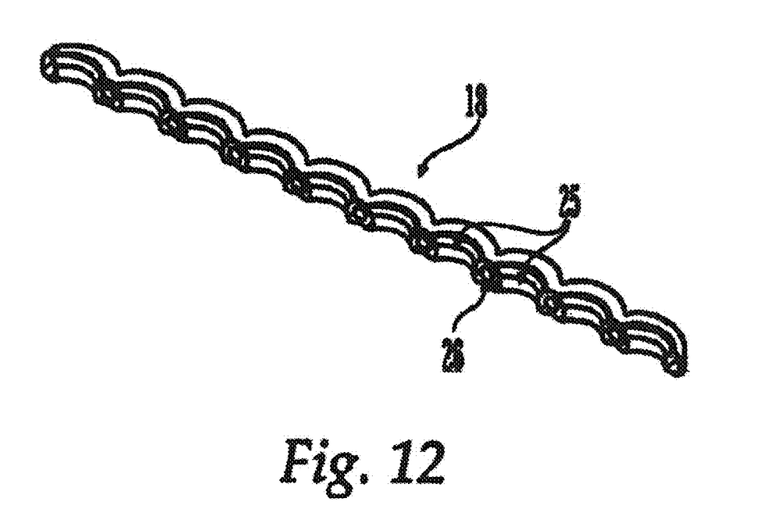
FIG. 12 is a cross-sectional view of a reconstruction plate.
Figure 13:
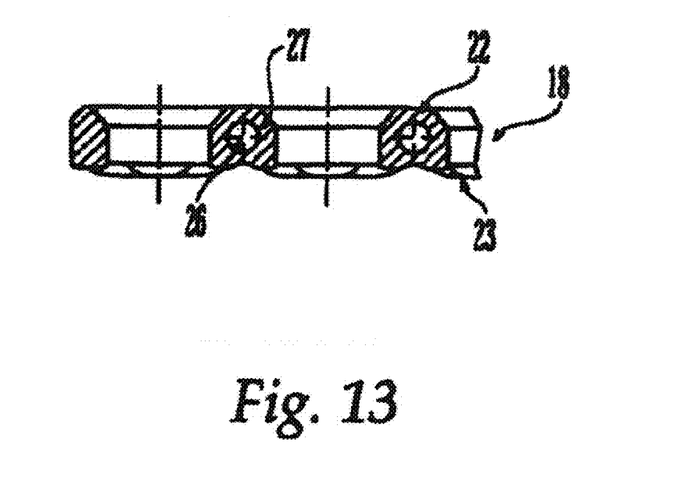
FIG. 13 is a partial side view of a reconstruction plate.

The reconstruction plates 18 may be constructed from any suitable bio-compatible material, including, but not limited to, titanium, alloys of titanium, stainless steel, resorbable materials, radio-translucent materials, allograft materials and resorbable materials, although one of ordinary skill in the art will know and appreciate that any biocompatible material may be used. The reconstruction plates 18 may comprise a plurality of generally perpendicular plate holes 25 which pass through the upper and lower surfaces of plate 18 and are generally perpendicular to the longitudinal axis for receiving bone anchors. The reconstruction plates 18 may further comprise a plurality of holes or bores 26 disposed generally transversely to the generally perpendicularly disposed plate holes 25. Typically, the reconstruction plates 18 comprise from about 2 to about 26 generally perpendicular plate holes 25 and from about 1 to about 25 transverse holes or bores 26. As shown in FIG. 10, an overhead view of the reconstruction plate 18, the generally perpendicular plate holes 25 are generally uniform in shape and size, and preferably are circular holes with a diameter of from about 2 mm to about 9 mm, more preferably from about 4 mm to about 6 mm. In another embodiment the holes may be oblong and may be ramped to provide compression. The generally perpendicular plate holes may be configured to lock with an optionally supplied bone fastener. In FIG. 11, which shows a side view of reconstruction plate 18, the transverse plate holes 26 are disposed between adjacent generally perpendicular plate holes 25. FIG. 12 shows a cross-sectional view of reconstruction plate 18, wherein the location of the transverse plate holes 26 between adjacent generally perpendicular holes 25 can be seen. Transverse plate holes 26 typically have a diameter smaller than that of the generally perpendicular holes 25. Preferably, the transverse plate holes 26 have a diameter of from about 0.7 mm to about 2.5 mm, and more preferably about 1 mm. The diameter of the transverse plate holes 26 preferably is selected so as to accommodate the flexible cable 1. Typically, the reconstruction plate 18 is counter-bored at the location of each transverse hole 26. FIG. 13 shows a side view of a reconstruction plate 18, with transverse hole 26 and counter-bore 27.

As shown in FIGS. 10 to 13, both the generally perpendicular plate holes 25 and transverse plate holes 26 may be round and cylindrical. This preferred geometry minimizes the change in material properties in the areas near the plate holes. In one embodiment, generally perpendicular plate holes 25 are countersunk toward either the upper or the lower surface 22, 23 of the reconstruction plate 18. In a preferred embodiment, the generally perpendicular plate holes 25 are countersunk toward both the upper and the lower surface 22, 23 of the reconstruction plate 18. Countersunk generally perpendicular plate holes 25 better accommodate the heads of the cannulated bone screws 13, resulting in a highly stable system. In a preferred embodiment, the countersinks are in the shape of a cone.

In one embodiment the upper and lower surfaces 22, 23 of the reconstruction plate 18 are planar. Because of the symmetry of the bone plate 18, the bone plate 18 can be attached with either upper or lower surface 22, 23 facing the bone with identical clinical results. In a preferred embodiment, at least one reconstruction plate 18 is attached to the sternum on opposite sides of the sternal fragments.

The use of flexible cable 1, reconstruction plates 18 and cannulated screws 13 may be necessary in more complicated sternal reconstruction procedures, such as procedures wherein both midline and transverse fractures must be addressed. The reconstruction plates 18 can be attached to each side of the split sternum by cannulated screws 13. Flexible cable or wire 1 may then be used to align and reduce the sternum. If transverse fractures are present, the reconstruction plates 18 function to reduce such fractures. Without being bound by theory, it is believed that the cannulations 16 in the screw 13 and the transverse holes 26 in the reconstruction plates 18 provide improvements to the Chase technique, which is described in "Internal Fixation of the Sternum in Median Sternotomy Dehiscence," Chase et al., Plastic and Reconstructive Surgery, May 1999, the contents of which are incorporated herein as if fully set forth.

In one embodiment, one end of the flexible cable 1 comprises a preinstalled flattened round crimp fitting 2 with a diametrical hole or bore 6 through which the second or thermally fused end 8 of the flexible cable 1 may pass after the flexible cable 1 is looped around the sternum or passes through the cannulated screws 13 and/or through the reconstruction plates 18 and throughbores 16 of the cannulated screws 13. In this embodiment, the separated parts of the sternum may be reapproximated by tensioning the flexible cable 1 to a desired tension, and securing the flexible cable 1 by crimping. In one embodiment, a cylindrical ferrule 9 may be crimped onto flexible cable 1 after the cable 1 is drawn through the hole 6 in crimp fitting 2 to the preselected desired tension. The safety cable tool described above may be used to achieve such tensioning and crimping.

The present invention also relates to a sternal reconstruction kit which comprises at least one flexible cable 1, at least one or more cannulated screws 13 and at least one or more reconstruction plates 18. Optionally the kit may contain at least one flexible cable 1, wherein the second or thermally fused end 8 of the flexible cable 1 may be attached to a suture 11. Further, the kit may optionally comprise a plurality of sizes of cannulated screws 13 and/or a plurality of sizes of reconstruction plates 18. In a preferred embodiment, the reconstruction kit comprises at least one ferrule 9. The inner diameter of the ferrule 9 may have a sharp edge in order to facilitate the cutting of the flexible cable 1 during crimping of the ferrule 9 onto the flexible cable 1.

While various descriptions of the present invention are described above, it should be understood that the various features can be used singly or in any combination thereof. Therefore, this invention is not to be limited to only the specifically preferred embodiments depicted herein. Further, it should be understood that variations and modifications within the spirit and scope of the invention may occur to those skilled in the art to which the invention pertains. For example, fixation of a sternum may be effected by use of a flexible cable 1 and crimp fitting 2 alone, and/or in combination with cannulated screws 13 and/or further in combination with sternal reconstruction plates 18. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. A sternal reconstruction system for securing parts of a sternum comprising:
    a flexible cable having first and second ends;
    a crimp fitting member having first and second portions, the first portion having a crimp shaft extending longitudinally from the second portion and being attached to the first end of the flexible cable, and the second portion having a crimp head and a hole in the crimp head that is perpendicular to the crimp shaft and adapted to slidably receive the second end of the flexible cable;
    at least one cannulated screw having a cannulation adapted to slidably receive the first portion of the crimp fitting member; and
    at least one reconstruction plate having at least one plate hole that slidably receives the at least one cannulated screw or the first portion of the crimp fitting member.

2. The sternal reconstruction system of claim 1, wherein the crimp head comprises a preinstalled flattened disk-like crimp head having a diameter of from about 2 mm to about 10 mm and a thickness of from about 0.1 mm to about 4 mm.

3. The sternal reconstruction system of claim 2, wherein the crimp fitting member is constructed from a material selected from the group consisting of titanium, alloys of titanium, stainless steel and resorbable materials.

4. The sternal reconstruction system of claim 2, wherein the crimp head is round.

5. The sternal reconstruction system of claim 2, wherein the crimp head is square, rectangular or other polygon shape.

6. The sternal reconstruction system of claim 2, wherein the crimp head comprises an upper surface and a lower surface.

7. The sternal reconstruction system of claim 6, wherein the upper surface of the crimp head has rounded edges.

8. The sternal reconstruction system of claim 6, wherein the lower surface of the crimp head is designed to mate with a top surface of the at least one cannulated screw or reconstruction plate.

9. The sternal reconstruction system of claim 6, wherein the lower surface of the crimp head is flat.

10. The sternal reconstruction system of claim 2, wherein the hole in the crimp head extends diametrically across the crimp head.

11. The sternal reconstruction system of claim 10, wherein the crimp shaft extends perpendicularly from the lower surface of the crimp head.

12. The sternal reconstruction system of claim 11, wherein the crimp shaft is surrounded by the lower surface of the crimp head such that the perimeter of the lower surface of the crimp head provides an annular bearing surface and the width of the annular bearing surface is from about 0.5 mm to about 3 mm.

13. The sternal reconstruction system of claim 6, wherein the the crimp shaft extends perpendicular to the lower surface of the crimp head.

14. The sternal reconstruction system of claim 13, wherein the crimp shaft is cylindrically shaped.

15. The sternal reconstruction system of claim 13, wherein the crimp shaft has a non-circular cross-section.

16. The sternal reconstruction system of claim 15, wherein the non-circular cross-section of the crimp shaft engages a non-circular recess formed in the at least one cannulated screw and prevents rotation of the crimp fitting in the cannulation of the at least one cannulated screw.

17. The sternal reconstruction system of claim 13, wherein the crimp shaft is from about 0.7 mm to about 4 mm in diameter, and from about 1.5 mm to about 4 mm in length.

18. The sternal reconstruction system of claim 17, wherein the crimp shaft is sized and shaped so as to fit within the cannulation or the at least one plate hole.

19. The sternal reconstruction system of claim 1, wherein the flexible cable having first and second ends is a multi-wire stranded cable.

20. The sternal reconstruction system of claim 1, wherein the flexible cable is Cerclage wire.

21. The sternal reconstruction system of claim 1, wherein the second end of the cable further comprises a suture.

22. The sternal reconstruction system of claim 21, wherein the suture is constructed from a material selected from the group consisting of titanium, alloys of titanium and stainless steel.

23. The sternal reconstruction system of claim 21, wherein the suture is designed to be removable.

24. The sternal reconstruction system of claim 1, wherein the flexible cable is constructed from a material selected from the group consisting of titanium, alloys of titanium, stainless steel and resorbable materials.

25. The sternal reconstruction system of claim 1, wherein the reconstruction plate has a longitudinal axis and comprises an upper and a lower surface, and the at least one plate hole passes through the upper and lower surfaces and generally perpendicular to the longitudinal axis for receiving a bone anchor, the at least one reconstruction plate further including at least one bore disposed transverse to the generally perpendicularly disposed plate hole.

26. The sternal reconstruction system of claim 25, wherein the at least one reconstruction plate comprises a plurality of holes passing through the upper and lower surfaces and generally perpendicular to the longitudinal axis for receiving bone anchors.

27. The sternal reconstruction system of claim 26, further comprising a plurality of bores disposed transverse to the generally perpendicularly disposed plate holes.

28. The sternal reconstruction system of claim 27, wherein the plurality of holes passing through the upper and lower surfaces and generally perpendicular to the longitudinal axis are round and cylindrical.

29. The sternal reconstruction system of claim 28, wherein the plurality of holes passing through the upper and lower surfaces and generally perpendicular to the longitudinal axis are countersunk toward either the upper or the lower surfaces of the reconstruction plate.

30. The sternal reconstruction system of claim 28, wherein the plurality of holes passing through the upper and lower surfaces and generally perpendicular to the longitudinal axis are countersunk toward both the upper and the lower surfaces of the reconstruction plate.

31. The sternal reconstruction system of claim 30, wherein the plurality of holes are countersunk in the shape of a cone.

32. The sternal reconstruction system of claim 28, wherein the upper and lower surfaces of the reconstruction plate are planar.

33. The sternal reconstruction system of claim 28, wherein the reconstruction plate is constructed from a material selected from the group consisting of titanium, alloys of titanium, stainless steel, resorbable materials, radio-translucent materials, allograft materials and resorbable materials.

34. The sternal reconstruction system of claim 27, wherein the plurality of bores disposed transverse to the generally perpendicularly disposed plate holes are round and cylindrical.

35. The sternal reconstruction system of claim 27, wherein the generally transverse bores are each independently angled at a solid angle of from 0° to about 30° from normal to side surfaces of the reconstruction plate.

36. The sternal reconstruction system of claim 35, wherein the generally transverse bores are each independently angled at an angle of from 0° to about 30° from normal to the side surfaces of the reconstruction plate and transverse to the longitudinal axis.

37. The sternal reconstruction system of claim 35, wherein the generally transverse bores are normal to the side surfaces of the reconstruction plate.

38. The sternal reconstruction system of claim 26, wherein the generally perpendicular plate holes are each independently angled at a solid angle of from 0° to about 30° from normal to the upper and lower surfaces of the reconstruction plate.

39. The sternal reconstruction system of claim 38, wherein the generally perpendicular plate holes are each independently angled at an angle of from 0° to about 30° from normal to the upper and lower surfaces of the reconstruction plate and along the longitudinal axis.

40. The sternal reconstruction system of claim 38, wherein the generally perpendicular holes are normal to the upper and lower surfaces of the reconstruction plate.

41. The sternal reconstruction system of claim 26, wherein the plurality of generally perpendicular plate holes are configured to lock with a bone fastener.

42. The sternal reconstruction system of claim 1, further comprising at least two reconstruction plates.

43. The sternal reconstruction system of claim 1, wherein the at least one cannulated screw is selected from the group consisting of a locking and a non-locking screw.

44. The sternal reconstruction system of claim 43, wherein the at least one cannulated screw is at least partially threaded for attachment to bone.

45. The sternal reconstruction system of claim 43, wherein the at least one cannulated screw is constructed from a material selected from the group consisting of titanium, alloys of titanium, stainless steel and resorbable materials.

46. The sternal reconstruction system of claim 43, wherein the at least one cannulated screw comprises a head having a top surface, wherein the top surface may be curved, substantially flat or have other complex geometry.

47. The sternal reconstruction system of claim 1, wherein the flexible cable is secured to the second portion of the crimp fitting member by deforming the second portion of the crimp fitting member.

48. The sternal reconstruction system of claim 1, wherein the cannulation of the at least one cannulated screw slidably receives the first portion of the crimp fitting member.

49. A sternal reconstruction kit comprising:
a plurality of flexible cables, each of the plurality of flexible cables having a first end and a second end;
a plurality of crimp fitting members, each of the plurality of crimp fitting members having first and second portions, the first portion of each of the plurality of crimp fitting members having a crimp shaft extending longitudinally from the second portion and being attached to the first end of one of the plurality of flexible cables, and the second portion of each of the plurality of crimp fitting members having a crimp head and a hole in the crimp head that is perpendicular to the crimp shaft and adapted to slidably receive the second end of one of the plurality of flexible cables;
a plurality of cannulated screws having different shapes or sizes, each of the plurality of cannulated screws having a cannulation adapted to slidably receive the first portion of one of the plurality of crimp fittings; and
a plurality of reconstruction plates having different shapes or sizes, each of the plurality of reconstruction plates having at least one plate hole that slidably receives one of the plurality of cannulated screws or the first portion of one of the plurality of crimp fittings.

50. The sternal reconstruction kit of claim 49, wherein second end of one of the plurality of flexible cables is attached to a suture.

51. The sternal reconstruction kit of claim 49, wherein the hole in the crimp head of at least one crimp fitting member extends diametrically through the crimp head.

52. The sternal reconstruction kit of claim 51, further comprising at least one ferrule and wherein the at least one ferrule is adapted to be crimped onto one of the plurality of flexible cables, and the inner diameter of the at least one ferrule comprises a sharp edge in order to facilitate the cutting of one of the plurality of flexible cables during crimping of the ferrule.

53. The sternal reconstruction system of claim 49, wherein the plurality of flexible cables are secured to the second portion of the plurality of crimp fitting members by deforming the second portion of the plurality of crimp fitting members.

* * * * *